United States Patent
Valkonen

(10) Patent No.: US 10,451,562 B2
(45) Date of Patent: Oct. 22, 2019

(54) MACHINE VISION METHOD AND SYSTEM

(71) Applicant: Procemex Oy, Jyväskylä (FI)

(72) Inventor: Mika Valkonen, Äänekoski (FI)

(73) Assignee: Procemex Oy, Jyväskylä (FI)

( * ) Notice: Subject to any disclaimer, the term of this patent is extended or adjusted under 35 U.S.C. 154(b) by 0 days.

(21) Appl. No.: 16/093,724

(22) PCT Filed: Apr. 28, 2017

(86) PCT No.: PCT/FI2017/050322
§ 371 (c)(1),
(2) Date: Oct. 15, 2018

(87) PCT Pub. No.: WO2017/191361
PCT Pub. Date: Nov. 9, 2017

(65) Prior Publication Data
US 2019/0137410 A1 May 9, 2019

(30) Foreign Application Priority Data
May 6, 2016 (FI) .................................. 20165389

(51) Int. Cl.
| | |
|---|---|
| *H04N 9/47* | (2006.01) |
| *H04N 7/18* | (2006.01) |
| *G01N 21/89* | (2006.01) |
| *G01N 29/14* | (2006.01) |
| *G01N 21/898* | (2006.01) |

(Continued)

(52) U.S. Cl.
CPC ......... *G01N 21/89* (2013.01); *G01N 21/8901* (2013.01); *G01N 21/8983* (2013.01); *G01N 29/14* (2013.01); *G05B 23/0297* (2013.01); *G06T 7/0004* (2013.01); *H04N 5/23203* (2013.01); *G05B 2219/37208* (2013.01); *G05B 2219/37337* (2013.01); *G06T 2207/30164* (2013.01)

(58) Field of Classification Search
USPC ........................................... 348/92, 154, 155
See application file for complete search history.

(56) References Cited

U.S. PATENT DOCUMENTS

| | | | | |
|---|---|---|---|---|
| 7,983,933 B2 * | 7/2011 | Karkanias | .............. | G06Q 10/02 705/2 |
| 8,213,685 B2 * | 7/2012 | Wang | ........................ | G06T 7/20 340/933 |

(Continued)

FOREIGN PATENT DOCUMENTS

WO       2007096475 A1       8/2007

*Primary Examiner* — Nigar Chowdhury
(74) *Attorney, Agent, or Firm* — Berggren LLP

(57) ABSTRACT

The invention relates to a method, comprising capturing an image of an object to be monitored at a first image capturing frequency by an image sensor of a machine vision system, transmitting said captured image data to an image data processing device and analyzing said received image data by said image data processing device, and wherein if the image data is detected to comprise a deviation, a trigger signal is transmitted for triggering an image sensor for reconfiguring it to capture an image burst and for transmitting the captured image burst data to said image data processing device for further analysis. The invention further relates to a machine vision system and a computer program product performing the method.

15 Claims, 2 Drawing Sheets

(51) Int. Cl.
*G05B 23/02* (2006.01)
*G06T 7/00* (2017.01)
*H04N 5/232* (2006.01)
H04N 5/253 (2006.01)
H04N 3/36 (2006.01)
H04N 9/11 (2006.01)

(56) References Cited

U.S. PATENT DOCUMENTS 9,245,187 B1 * 1/2016 Varghese ........... G06K 9/00771
10,205,913 B2 * 2/2019 Smith ................. H04N 5/23206
10,365,716 B2 * 7/2019 Aimone ................. G09G 3/003
2002/0109112 A1 8/2002 Guha
2005/0276445 A1 12/2005 Silver
2012/0013733 A1 1/2012 Koltermann
2015/0039250 A1 2/2015 Rank

* cited by examiner

MACHINE VISION METHOD AND SYSTEM

PRIORITY

This application is a U.S. national application of the international application number PCT/FI2017/050322 filed on Apr. 28, 2017 and claiming priority of Finnish national application FI20165289 filed on May 6, 2016 the contents of all of which are incorporated herein by reference.

TECHNICAL FIELD

The present invention relates to a method for imaging of continuous manufacturing processes, in which method a camera is used for burst mode imaging of an object to be monitored.

The invention also relates to a system and a computer program product causing an apparatus to carry out the method.

BACKGROUND

In continuous manufacturing processes, there are materials or products constantly running through the machine. In such processes, the product must be monitored in order to detect possible deviations or web breaks. Furthermore, condition of the machine itself can be monitored in order to detect possible machine malfunctions or process deviations that may cause those above-mentioned deviations to products or web breaks, but which could also cause unscheduled or planned downtimes of a machine/machinery or damage the machine itself. By this kind of monitoring(s) it is possible to obtain a high quality end product. The product, machine or process may be monitored, for example, by machine vision systems such as camera systems. The captured images are analysed by a processing unit.

SUMMARY

Now there has been invented an improved method and technical equipment implementing the method. Various aspects of the invention include a method, a machine vision system comprising at least one image sensor and also possibly an acoustic sensor, and a computer readable medium comprising a computer program stored therein, which are characterized by what is stated in the independent claims. Various embodiments of the invention are disclosed in the dependent claims.

According to a first aspect of the invention, there is provided a method, comprising capturing an image of an object to be monitored at a first image capturing frequency by an image sensor of a machine vision system, transmitting said captured image data to a data processing device, and analysing said received image data by said data processing device, and wherein if said received image data is detected to comprise a deviation, said data processing device is arranged to transmit a trigger signal for triggering an image sensor so that at least one image sensor is reconfigured to capture an image burst at a second image capturing frequency and to transmit the captured image burst data to said data processing device for further analysis.

According to an embodiment, the method further comprises recording acoustic environment around the machine vision system, transmitting said recorded acoustic environment data to the data processing device, and analysing said received acoustic environment data by said data processing device, and wherein if said received acoustic environment data is detected to comprise a deviation, said data processing device is arranged to transmit a trigger signal for triggering an image sensor so that at least one image sensor is reconfigured to capture an image burst at the second image capturing frequency and to transmit the captured image burst data to said data processing device for further analysis. According to an embodiment, the method further comprises determining a root cause of the deviation, and determining the image sensor reconfigured to capture the image burst on the basis of the root cause. According to an embodiment, the image sensor continues capturing images at the first image capturing frequency after the image burst. According to an embodiment, the trigger signal determines image capturing frequency of the image burst. According to an embodiment, the trigger signal determines image resolution of images captured during the image burst. According to an embodiment, the trigger signal determines length of time of the image burst.

According to a second aspect of the invention, there is provided a machine vision system for monitoring an object to be monitored comprising an image sensor and a data processing device, wherein said image sensor is arranged to capture an image of said object to be monitored at a first image capturing frequency and to transmit said captured image data to the data processing device for analysing, and wherein if said received image data is detected to comprise a deviation, said data processing device is arranged to transmit a trigger signal for triggering an image sensor so that at least one image sensor is reconfigured to capture an image burst at a second image capturing frequency and to transmit the captured image burst data to said data processing device for further analysis.

According to an embodiment, the machine vision system further comprises an acoustic sensor, wherein said sensor is arranged to record acoustic environment around the machine vision system and wherein the acoustic sensor is further arranged to transmit said recorded acoustic environment data to the data processing device for analysing, and wherein if said received acoustic environment data is detected to comprise a deviation, said data processing device is arranged to transmit a trigger signal for triggering an image sensor so that at least one image sensor is reconfigured to capture an image burst at the second image capturing frequency and to transmit the captured image burst data to said data processing device for further analysis. According to an embodiment, the data processing device further determines a root cause of the deviation, and determines the image sensor reconfigured to capture the image burst on the basis of the root cause. According to an embodiment, the image sensor continues capturing images at the first image capturing frequency after the image burst. According to an embodiment, the trigger signal determines image capturing frequency of the image burst. According to an embodiment, the trigger signal determines image resolution of images captured during the image burst. According to an embodiment, the trigger signal determines length of time of the image burst.

According to a third aspect of the invention, there is provided a computer program product embodied on a non-transitory computer readable medium, comprising computer program code configured to, when executed on at least one processor, cause a system to capture an image of an object to be monitored at a first image capturing frequency by an image sensor of a machine vision system, transmit said captured image data to a data processing device, and analyse said received image data by said data processing device, and wherein if said received image data is detected to comprise a deviation, said data processing device is arranged to transmit a trigger signal for triggering an image sensor so that at least one image sensor is reconfigured to capture an image burst at a second image capturing frequency and to transmit the captured image burst data to said data processing device for further analysis.

According to an embodiment, the system further records acoustic environment around the machine vision system, transmits said recorded acoustic environment data to the data processing device, and analyses said received acoustic environment data by said data processing device, and wherein if said received acoustic environment data is detected to comprise a deviation, said data processing device is arranged to transmit a trigger signal for triggering an image sensor so that at least one image sensor is reconfigured to capture an image burst at the second image capturing frequency and to transmit the captured image burst data to said data processing device for further analysis. According to an embodiment, the system further determines a root cause of the deviation, and determines the image sensor reconfigured to capture the image burst on the basis of the root cause. According to an embodiment, the image sensor continues capturing images at the first image capturing frequency after the image burst. According to an embodiment, the trigger signal determines image capturing frequency of the image burst. According to an embodiment, the trigger signal determines image resolution of images captured during the image burst. According to an embodiment, the trigger signal determines length of time of the image burst.

BRIEF DESCRIPTION OF THE DRAWINGS

In the following, various embodiments of the invention will be described in more detail with reference to the appended drawings, in which.

DETAILED DESCRIPTION

Figure 1:
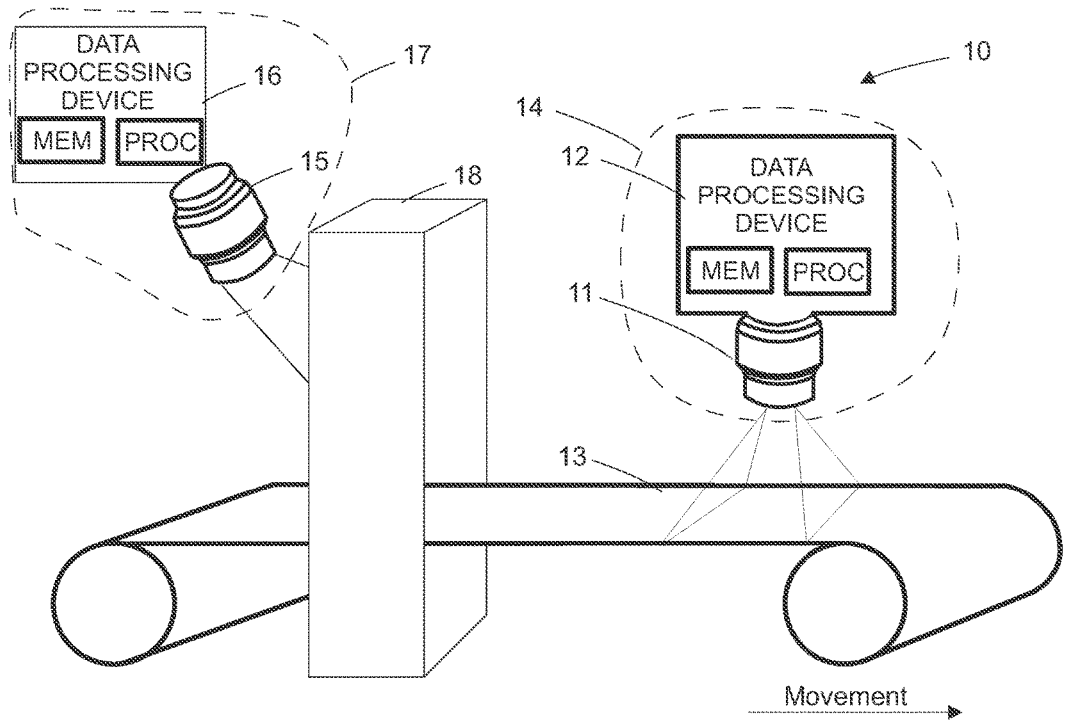
FIG. 1 shows a machine vision system according to an example embodiment.

The present invention relates to a machine vision system according to an example embodiment and comprising at least one image sensor used for detecting deviations in a web product, machinery or a process. The term "deviation" includes in this context any deviation detectable from the product, machinery or process, for example, a defect, a hole, a stain, a definite change, a grey or dark spot, a streak, a wrinkle, an air bubble or a pattern in a web, or a malfunction or fault or a defect or deviation in mechanical structure of a machine, or a defect or deviation in some other part of a process. The image sensor is used for capturing images of a moving object, for example, a web or a machine that is a monitoring target of that image sensor. The image sensor of the machine vision system may be, for example, a camera, for example, a c-mos or ccd camera, a matrix or line scan camera, a black and white or colour camera, a regular or smart camera, or any suitable camera. Targets arranged to be monitored may be illuminated for imaging. A machine vision system according to embodiments may be arranged, for example, in or in connection with web monitoring beams or web monitoring rails for supporting one or more image sensors and possible one or more lights.

Many deviations are such that one image or rarely captured sequential images of the deviation are not enough, but the product or machine must be monitored more carefully, for example, with a plurality of images with high frequency, in order to detect the whole deviation or to determine the root cause for the deviation. This means that more images of the deviation may be needed. Furthermore, condition of the machine itself may also need more accurate monitoring in order to enable detection of possible machine/machinery malfunction(s) or process deviations. This more accurate monitoring may again need a plurality of sequential images with high frequency.

The present invention further relates to a method according to an example embodiment of the invention, wherein one or more images of the web are captured by one or more image sensors at a first image capturing frequency in a so called first image capturing mode, and image data of one or more captured images are analysed by a data processing device of the image sensor and/or transmitted to an external data processing device for analysis. If one or more captured images are detected to comprise a deviation, at least one image sensor may be configured by a trigger signal to capture at least one image burst. The term "image burst" refers in this context a period of time during which an image sensor is in a high speed image shooting mode. Images captured during the image burst may also comprise at least partly overlapping image areas and they may also have higher resolution. The detected deviation may cause triggering of the same image sensor that captured the image comprising the deviation or one or more other image sensors instead of or in addition to that image sensor. The data processing device may, for example, by a trigger signal reconfigure an image sensor i.e. change a configuration of the image sensor so that the image sensor is configured to the second image capturing frequency mode that is the image burst mode. The trigger signal may also determine for the image sensor the image capturing frequency and/or a resolution of an image burst to be captured, how the images should overlap and/or length of time of the image burst.

Instead of or in addition to deviation detection of a material web, acoustic representation of process machinery may be analysed and at least one image sensor may also be configured by a trigger signal to capture at least one image burst in the second image capturing frequency mode, if a deviation, for example a predefined change, is detected in the acoustic representation of process machinery via an auditory analysis during the first image capturing mode. The auditory analysis may be performed, for example, by a data processing device of the image sensor and/or an external data processing device. The data processing device of the image sensor and/or an external data processing device may comprise an acquisition unit receiving the acoustic environment data of the process that is the environmental sound around the image sensors imaging the process and comprising acoustic sensor(s), such as a microphone recording acoustic environment i.e. audio signals around them.

Furthermore, at least one image sensor may also be triggered manually for capturing at least one image burst or one image sensor may also be triggered more than one image bursts by one trigger signal so that there are a predetermined interval between image bursts.

During image bursts one or more triggered image sensors are in the second image capturing frequency mode. The image capturing frequency of the second image capturing frequency mode is higher than the image capturing frequency of the first image capturing frequency mode. During the first image capturing frequency mode, an image sensor may capture, for example, 50-100 images per second and during the second image capturing frequency mode the image sensor may capture, for example, 500-1000 images per second. Usually, an image burst takes a relatively short time, for example, 0.5-1 second, because it may produce so much image data for analysing. Furthermore, images of the image burst may have higher resolution than images captured outside the image burst i.e. outside the second image capturing frequency mode i.e. during the first image capturing frequency mode. An image sensor suitable for capturing and also transmitting image burst data comprising a plurality of images, possibly high resolution images, needs to have sufficient processing power. The image sensor capturing the image burst may store image burst data in its memory before it transmits the image burst data for analysing to a data processing device, for example, an external data processing device that is wirelessly, or via a wired connection connected to the image sensor. This way, the data transmission rate may not form a limitation for image burst data transmission.

It may be predefined for the machine vision system or directly for one or more image sensors of the machine vision system which one or more image sensors are triggered to capture the image burst or alternatively the image sensor or the external data processing device may determine image sensor(s) used for image burst in the triggering signal.

The image sensor triggered for capturing an image burst may be defined, for example, as follows. The image sensor(s) may be determined on the basis of a detected deviation in a material web. The machine vision system may define inter-relationships between material web deviations and their root causes. There may be root causes for certain types of deviation that are stored in the memory of the data processing system. Further, on the basis of the root cause the machine vision system may determine one or more image sensors that are in such location(s) that the root cause or an area wherein the root cause causes deviation(s) should be imaged more carefully by the image burst. Furthermore, instead of or in addition to deviation detection of the material web, an image sensor for capturing an image burst may be determined on the basis of detected deviation in the acoustic representation of the machinery. A data processing device of the machine vision system may again define inter-relationships between deviation(s) of the acoustic representation of the machinery and their root causes. Again, on the basis of the root cause(s) the data processing device may determine one or more image sensors that are in a location of the root cause of the deviation e.g. near a certain machine or an area wherein the root cause causes changes in the acoustic representation of the machinery. It is possible that root causes of deviations are predefined for the machine vision system.

FIG. 1 shows an embodiment of the invention, in which a machine vision system 10 is disclosed in conjunction with an object to be monitored 13. The machine vision system comprises at least two smart cameras 14, 17 comprising an image sensor 11, 15 and a data processing device part 12, 16. The area image sensor 11 is arranged to capture images from an object to be monitored i.e. that is a movable web-like material and to transmit image data of each image to the data processing device part 12 of the smart camera 14. The area image sensor 15 is arranged to capture images from an object to be monitored i and to transmit image data of each image to the data processing device part 16 of the smart camera 17.

The data processing device part 12, 16 comprises at least one processor, at least one memory including computer program code for one or more program units, and means for receiving image data wirelessly or via wired connection from the sensor 11, for example, a receiver or a transceiver, and means for transmitting trigger signals wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and nonvolatile memory such as a hard disk for permanently storing data and programs. The data processing device part 12 of the smart camera 14 and the data processing device part 16 of the smart camera 17 may be any computing device suitable for handling image data such as a computer. The data processing device part 12, 16 is in electronic communication with the area image sensor 11, 15 via signal lines respectively. The smart camera 14, 17 may also include a video controller and an audio controller for generating signals that can be produced for the user with computer accessories. The smart camera 14, 17 produces output to the user through output means. The video controller may be connected to a display. The display may be e.g. a flat panel display or a projector for producing a larger image. The audio controller may be connected to a sound source, such as loudspeakers or earphones. The smart camera 14, 17 may also include an acoustic sensor such as a microphone.

The data processing device part 12, 16 is configured to receive from the image sensor 11, 15 images captured at a first image capturing frequency by the image sensor 11, 15 as image data. The data processing device parts 12, 16 analyse the above-mentioned images, and if, for example, the data processing device part 12 detects a deviation, it may configure by a trigger signal the image sensor 11 or alternatively the second image sensor 15 of the second camera 16, or both, by indicating that an image burst should be captured and the image burst data should be transmitted to the data processing device part 12, 16 for further analysis i.e. the data processing device part 12 requests an image burst from the image sensor 11 and/or from the image sensor 15 to the processing device part 16. During image burst, the image sensor(s) 11 and/or 15 capture images at the second image capturing frequency that is higher than the first image capturing frequency. The data processing device part 12 may also define in the trigger signal the number of images of image burst or the duration of the image burst for the image sensor(s) 11 and/or 15 or it may be predefined for the image sensor(s) 11 and/or 15. After the image sensor(s) 11 and/or 15 have captured the requested image burst, the image sensor(s) 11 and/or 15 start to capture images at the first image capturing frequency and transmit the image data until the next image burst trigger signal is received. In this embodiment, the second image sensor 15 capture images of an object to be monitored that is a machine 18 is arranged before the image sensor 11 in the process line.

Further, because the machine 18 is earlier in the process than the location where the deviation was found by image sensor 11, it is possible, for example, to check if the machine 18 is working properly or if the machine 18 is causing deviations to the material web. The data processing device part 12 may further be arranged to notify a user of the machinery comprising the machine vision system 10.

Figure 2:
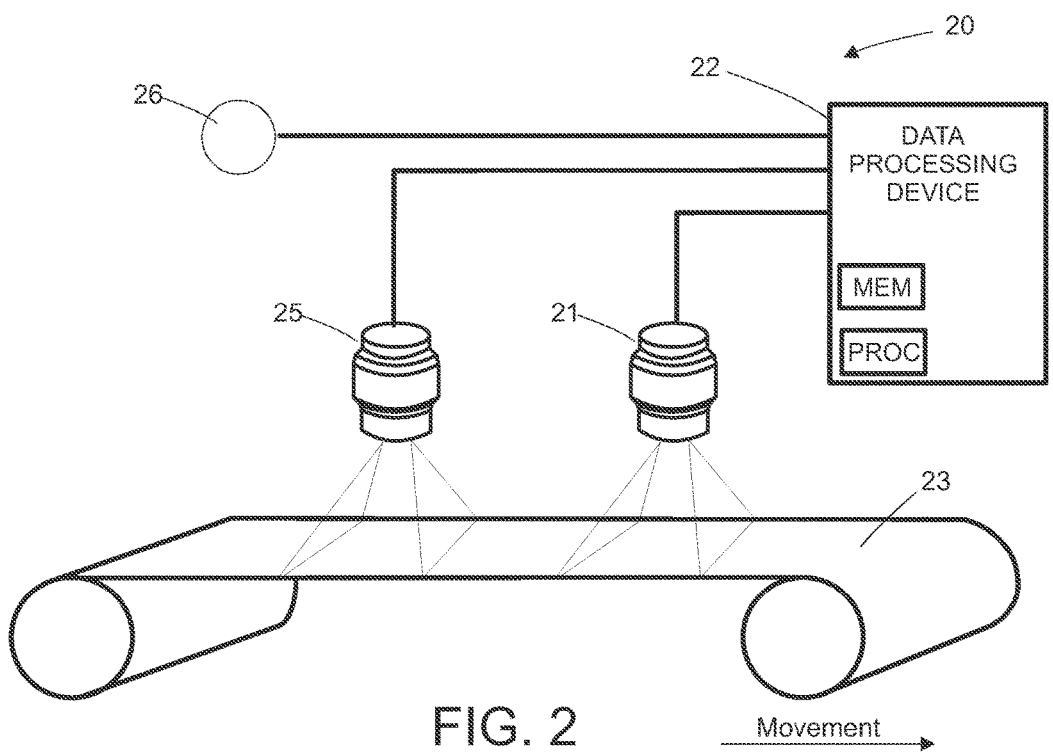
FIG. 2 shows a machine vision system according to an example embodiment.

FIG. 2 shows an embodiment of the invention, in which a machine vision system 20 is disclosed in conjunction with a moving object to be monitored 23. The machine vision system comprises at least two image sensors 21, 25, an acoustic sensor 26 and a data processing device 22 for processing acoustic data and image data. The image sensors 21, 25 are arranged to capture images from the moving object 23 that is a material web and to transmit data of each image to the data processing device 22. The acoustic sensor 26 is arranged to capture acoustic data around the moving object to be monitored 23.

The data processing device 22 comprises at least one processor, at least one memory including computer program code for one or more program units, and means for receiving image data wirelessly or via wired connection, for example, a receiver or a transceiver, and means for transmitting configurations by trigger signals wirelessly or via wired connection, for example, a transmitter or a transceiver. There may be multiple processors e.g. a general purpose processor and a graphics processor and a DSP processor and/or multiple different memories e.g. volatile memory for storing data and programs at run-time, and nonvolatile memory such as a hard disk for permanently storing data and programs. The data processing device 22 may be any computing device suitable for handling image data, such as a computer. The data processing device 22 is in electronic communication with the image sensors 21, 25 and the acoustic sensor 26 via signal lines. For handling the signals to/from the signal lines, the data processing device 22 comprises I/O circuitry. The connection between the image sensors 21, 25 and the acoustic sensor 26 and the data processing device 22 and the acoustic sensor 26 and the data processing device 22 are a wired or wireless network. The data processing device 22 may also include a video controller and an audio controller for generating signals that can be produced to the user with computer accessories. The video controller may be connected to a display. The display may be e.g. a flat panel display or a projector for producing a larger image. The audio controller may be connected to a sound source, such as loudspeakers or earphones. The data processing device 22 may also include an acoustic sensor, such as a microphone.

The data processing device 22 is configured to receive images captured at a first image capturing frequency from the image sensors 21, 25 and acoustic data captured by the acoustic sensor 26. The data processing device 22 analyses the above mentioned images and acoustic data and if the data processing device 22 detects a deviation, it may configure by a trigger signal the image sensor 21 or alternatively the second image sensor 25 or both by indicating that an image burst should be captured and image burst data should be transmitted to the data processing device 22 for further analysis i.e. the data processing device 22 requests an image burst from the image sensor 21 and/or from the image sensor 25. During image burst, the image sensor(s) 21 and/or 25 capture images at the second image capturing frequency that is higher than the first image capturing frequency.

In this embodiment, the second image sensor 25 is arranged before the image sensor 21 in the process line for imaging the object to be monitored 23. Thus, if the data processing device 22 detects a deviation in an image data received from image sensor 21, it is possible that there is something wrong in the moving object to be monitored 23 already in the earlier phase of the process and the second image sensor 25 is triggered to perform an image burst.

The data processing device 22 may also define the number of images of image burst or the duration of the image burst for the image sensor(s) 21 and/or 25 or it may be predefined for the image sensor(s) 21 and/or 25. After the image sensor(s) 21 and/or 25 have captured and image data have been transmitted the requested image burst data, the image sensor(s) 21 and/or 25 start to capture and at the first image capturing frequency until the next image burst trigger signal is received. The data processing device 22 may further be arranged to notify a user of the machine comprising the machine vision system 20.

Some image sensors may also offer a possibility of having multiple predetermined configuration sets, which if used can speed up the process of re-configuring the image sensor 21, 25 to the different modes. In the case of predetermined configuration sets, instead of a list of parameters, a simple command from the data processing device 22 will be enough to re-configure the image sensor 21, 25 to perform the image burst. It is also possible that the image sensor switch to an image burst mode automatically without a trigger signal or any other command, for example, at predetermined times.

It is also possible that several image burst mode types are used in one machine vision system, for example, used image capturing frequencies or image burst lengths or number of image bursts may vary and they may depend, for example, on a root cause of a deviation or an imaging target. Again the a data processing device may determine for an image sensor what image burst mode to use, for example, by a triggering signal or the type of an image burst mode may be predetermined for each image sensor(s) beforehand. If the image burst mode type is predetermined beforehand, it may be enough to receive just a simple trigger signal indicating a need to change to an image burst state mode.

Figure 3:
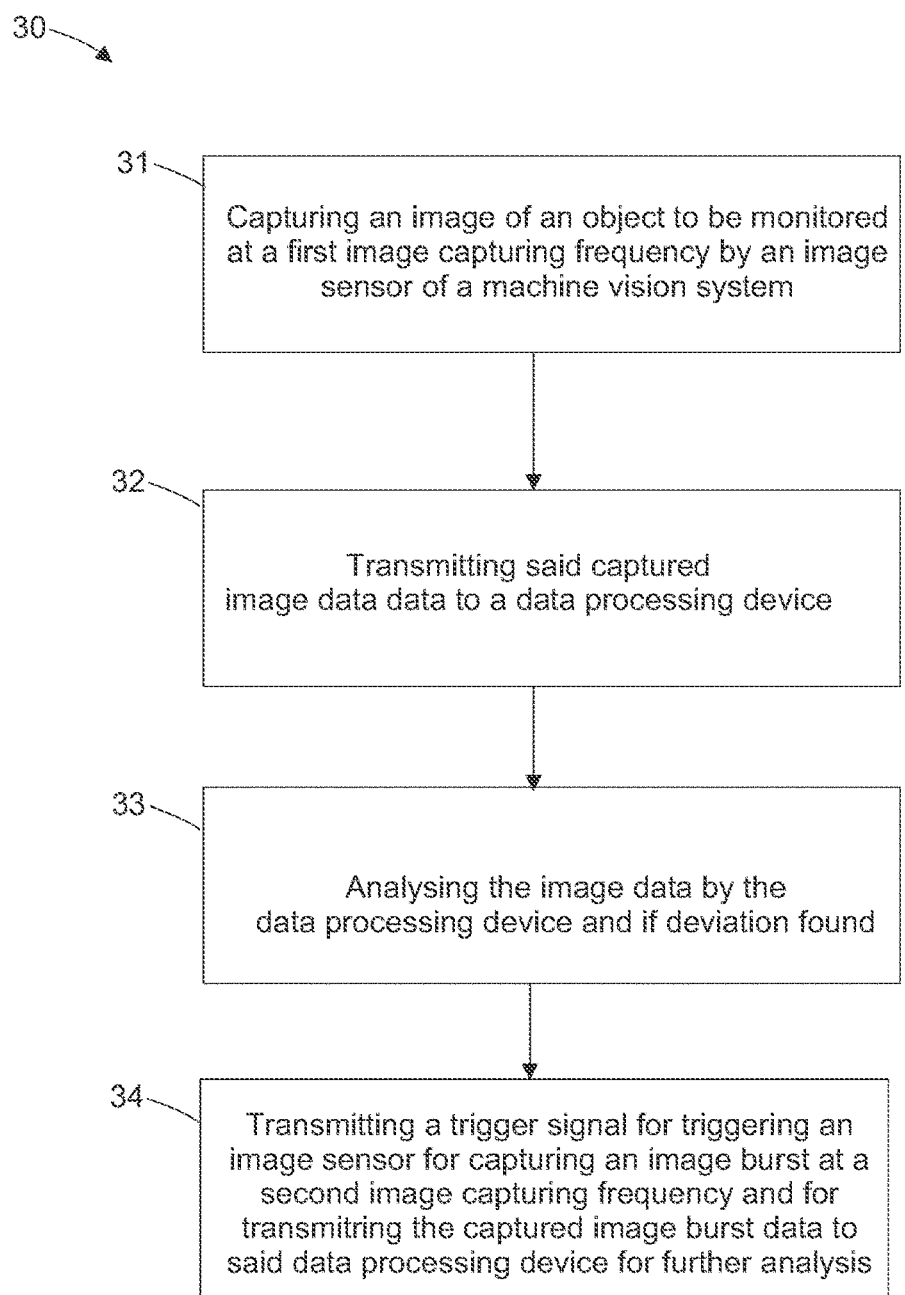
FIG. 3 shows an inspection method of a machine vision system according to an example embodiment.

FIG. 3 shows a deviation inspection method 30 of a machine vision system according to an example embodiment. In step 31 an image sensor of a machine vision system captures an image of an object to be monitored at a first image capturing frequency. In step 32 an image data processing device transmits the captured image data to an image data processing device. In step 33 the image data processing device analyses the received image data and if said received image data is detected to comprise a deviation, the image data processing device, in step 34, transmits a trigger signal for triggering an image sensor so that at least one image sensor is reconfigured to capture an image burst at a second image capturing frequency and to transmit the captured image burst data to said image data processing device for further analysis. It should be noted that image sensors may also be used for imaging other type of moving object(s) than web-like material.

The various embodiments of the invention can be implemented with the help of computer program code that resides in a memory and causes an apparatus to carry out the invention. For example, the apparatus that is a computing device, for example, a data processing device may comprise circuitry and electronics for analysing, receiving and transmitting data, a computer program code in a memory, and a processor which, when running the computer program code, causes the apparatus to carry out the features of an embodiment. The processor, when running the computer program code, may carry out the steps of the following method: capturing image(s) of an object to be monitored by an image sensor, for example, a camera sensor, at a first image capturing frequency, transmitting image data of said captured images, analysing the received images, and if said received image is detected to comprise a deviation or if the acoustic representation of the machinery is detected to comprise change, said data processing device is arranged to transmit configurations by a trigger signal to at least one image sensor, and wherein said at least one image sensor is arranged to capture an image burst that is imaging at a second image capturing frequency during a relatively short period of time. After the image burst, the image sensor continues to image at the first image capturing frequency. The method may further the comprise the following steps, wherein the data processing device is arranged to store and transmit image data of said image burst to the data processing device for further analysis. It should be noted that there may not always need to be a defect in an image or a change in acoustic representation of the machinery so that the data processing device triggers an image burst, but the image burst may also be triggered randomly by the data processing device.

Considerable advantages are achieved by the present invention when compared to methods and systems of existing machine vision systems comprising at least an image sensor e.g. a camera suitable for capturing image bursts. By means of the arrangement according to the invention it is possible to use an image sensor at two different modes, wherein the first mode comprises imaging at a first image capturing frequency and the second mode comprises imaging at a second image capturing frequency for short period of time, when needed. In addition, by means of the arrangement according to the invention it is also possible to provide the image burst data whenever needed, for example, when individual and less frequently captured images do not give enough information.

It is obvious that the present invention is not limited solely to the above-presented embodiments, but it can be modified within the scope of the appended claims.

The invention claimed is:

1. A method, comprising steps of:
   capturing an image of an object to be monitored at a first image capturing frequency by an image sensor of a machine vision system;
   transmitting captured image data to a data processing device; and
   analysing said received image data by said data processing device, and wherein
   if said received image data is detected to comprise a deviation, said data processing device is arranged to transmit a trigger signal for triggering at least the image sensor that captured the image data comprising the deviation so that at least that image sensor is reconfigured to capture an image burst at a second image capturing frequency, wherein the trigger signal defines the duration of the image burst, and wherein the second image capturing frequency of the image burst is higher than the first image capturing frequency, and to transmit the captured image burst data to said data processing device for further analysis.

2. The method according to claim 1, wherein the method further comprises a steps of:
   recording acoustic environment around machine vision system;
   transmitting said recorded acoustic environment data comprising acoustic representation of process machinery to the data processing device; and
   analysing said received acoustic environment data by said data processing device, and wherein
   if said received acoustic environment data is detected to comprise a change in the acoustic representation of process machinery during the first image capturing mod, said data processing device is arranged to transmit a trigger signal for triggering an image sensor so that at least one image sensor is reconfigured to capture an image burst at the second image capturing frequency and to transmit the captured image burst data to said data processing device for further analysis.

3. The method according to claim 1, wherein the method further comprises steps of:
   defining inter-relationships between deviations of the object to be monitored and their causes;
   determining a cause of the detected deviation; and
   determining the image sensor reconfigured to capture the image burst on the basis of the cause, wherein the image sensor is in such a location wherein the cause caused the detected deviation.

4. The method according to claim 1, wherein the image sensor continues capturing images at the first image capturing frequency after the image burst.

5. The method according to claim 1, wherein the trigger signal determines image capturing frequency of the image burst.

6. The method according to claim 1, wherein the trigger signal determines image resolution of images captured during the image burst.

7. The method according to claim 1, wherein the trigger signal determines length of time of the image burst.

8. A machine vision system for monitoring an object to be monitored comprising an image sensor and a data processing device, wherein said image sensor is arranged to capture an image of said object to be monitored at a first image capturing frequency and to transmit said captured image data to the data processing device for analysing, and wherein if said received image data is detected to comprise a deviation, said data processing device is arranged to transmit a trigger signal for triggering at least the image sensor that captured the image data comprising the deviation so that at least that image sensor is reconfigured to capture an image burst at a second image capturing frequency, wherein the trigger signal defines the duration of the image burst, and wherein the second image capturing frequency of the image burst is higher than the first image capturing frequency, and to transmit the captured image burst data to said data processing device for further analysis.

9. The machine vision system according to claim 8, wherein the machine vision system further comprises an acoustic sensor, wherein said acoustic sensor is arranged to record acoustic environment around the machine vision system and wherein the acoustic sensor is further arranged to transmit said recorded acoustic environment data comprising acoustic representation of process machinery to the data processing device for analysing, and wherein if said received acoustic environment data is detected to comprise a change in the acoustic representation of process machinery during the first image capturing mod, said data processing device is arranged to transmit a trigger signal for triggering an image sensor so that at least one image sensor is reconfigured to capture an image burst at the second image capturing frequency and to transmit the captured image burst data to said data processing device for further analysis.

10. The machine vision system according to claim 8, wherein the data processing device further:
    defines inter-relationships between deviations of the object to be monitored and their causes;
    determines a cause of the detected deviation; and
    determines the image sensor reconfigured to capture the image burst on the basis of the cause, wherein the image sensor is in such a location wherein the cause caused the detected deviation.

11. The machine vision system according to claim 8, wherein the image sensor continues capturing images at the first image capturing frequency after the image burst.

12. The machine vision system according to claim 8, wherein the trigger signal determines image capturing frequency of the image burst.

13. The machine vision system according to claim 8, wherein the trigger signal determines image resolution of images captured during the image burst.

14. The machine vision system according to claim 8, wherein the trigger signal determines length of time of the image burst.

15. A computer program product, stored on a computer readable medium and executable in a computing device, wherein the computer program product comprises instructions to perform a method according to claim 1.

* * * * *